US009999416B2

(12) United States Patent
Kelly et al.

(10) Patent No.: US 9,999,416 B2
(45) Date of Patent: Jun. 19, 2018

(54) METHODS AND APPARATUS FOR INTERNAL HIP DISTRACTION

(71) Applicant: Arthrex, Inc., Naples, FL (US)

(72) Inventors: Bryan Kelly, Riverside, CT (US); Reinhold Schmieding, Naples, FL (US); Ricardo Albertorio, Naples, FL (US); Kenneth Helenbolt, Naples, FL (US); John P. Gualdoni, Naples, FL (US)

(73) Assignee: Arthrex, Inc., Naples, FL (US)

( * ) Notice: Subject to any disclaimer, the term of this patent is extended or adjusted under 35 U.S.C. 154(b) by 296 days.

(21) Appl. No.: 14/838,662

(22) Filed: Aug. 28, 2015

(65) Prior Publication Data

US 2017/0055972 A1    Mar. 2, 2017

(51) Int. Cl.
| | | |
|---|---|---|
| *A61B 17/58* | (2006.01) | |
| *A61B 17/60* | (2006.01) | |
| *A61F 2/00* | (2006.01) | |
| *A61B 17/02* | (2006.01) | |
| *A61B 17/84* | (2006.01) | |

(52) U.S. Cl.
CPC .......... *A61B 17/025* (2013.01); *A61B 17/844* (2013.01); *A61B 2017/0275* (2013.01)

(58) Field of Classification Search
CPC combination set(s) only.
See application file for complete search history.

(56) References Cited

U.S. PATENT DOCUMENTS

| | | | |
|---|---|---|---|
| 6,755,865 | B2 | 6/2004 | Tarabishy |
| 8,672,947 | B2 | 3/2014 | Flom |
| 8,721,649 | B2 | 5/2014 | Gifford |
| 8,828,008 | B2 | 9/2014 | Stubbs |
| 8,858,563 | B2 | 10/2014 | Philippon et al. |
| 2007/0168036 | A1 | 7/2007 | Ainsworth et al. |
| 2009/0312807 | A1 | 12/2009 | Boudreault et al. |
| 2011/0152868 | A1 | 6/2011 | Kourtis et al. |
| 2011/0166579 | A1 | 7/2011 | Deem et al. |
| 2011/0282387 | A1 | 11/2011 | Suh et al. |
| 2012/0239046 | A1 | 9/2012 | Kaiser et al. |
| 2012/0240938 | A1 | 9/2012 | Pamichev |
| 2013/0053902 | A1* | 2/2013 | Trudeau ................ A61B 17/68 606/313 |
| 2013/0131444 | A1 | 5/2013 | Boudreault et al. |
| 2013/0231671 | A1 | 9/2013 | Boudreault et al. |
| 2014/0277185 | A1 | 9/2014 | Boileau et al. |
| 2014/0378982 | A1 | 12/2014 | Philippon et al. |

(Continued)

FOREIGN PATENT DOCUMENTS

| | | |
|---|---|---|
| WO | 99/37219 | 7/1999 |
| WO | 2006/135935 A1 | 12/2006 |

(Continued)

OTHER PUBLICATIONS

International Search Report and Written Opinion of the International Searching Authority for International Application No. PCT/US2016/047234 dated Jan. 30, 2017.

(Continued)

*Primary Examiner* — Sameh Boles
(74) *Attorney, Agent, or Firm* — Carlson, Gaskey & Olds

(57) ABSTRACT

This present invention relates to medical procedures and force application distraction devices for internal joint distraction.

15 Claims, 2 Drawing Sheets

(56) References Cited

U.S. PATENT DOCUMENTS

2015/0057668 A1 2/2015 Chehab et al.
2015/0196342 A1 7/2015 Suddaby

FOREIGN PATENT DOCUMENTS

WO  WO 2012/064786 A1  5/2012
WO     2013/052807 A2  4/2013

OTHER PUBLICATIONS

Stryker "Dynamic Joint Distractor II, External Fixation System." 2006.
International Preliminary Report on Patentability for International Application No. PCT/US2016/047234 dated Mar. 15, 2018.

* cited by examiner

METHODS AND APPARATUS FOR INTERNAL HIP DISTRACTION

BACKGROUND

This disclosure relates to surgical methods and devices for internal joint distraction. In particular, the device and method described herein utilize less force and cause less collateral damage than existing joint distraction systems.

SUMMARY

Disclosed herein are medical devices and methods for internally distracting joints by using minimally invasive distraction. Minimally invasive devices are deployed within a portion of a bone proximal to a bone joint, e.g., in the greater trochanter, and which allow direct force application to the joint to be distracted. The disclosed devices are used in medical procedures for treating/correcting/repairing damage/diseased articular joints, e.g., avascular necrosis of the hip, arthritis in younger people, femoral-cetabular impingements, etc.

In an illustrative embodiment, a method of distracting a bone joint is disclosed and includes forming a tunnel in one bone of a bone joint; arranging a fastener assembly in the tunnel; and applying a force directly to the fastener assembly to separate and distract the one bone from another bone of the bone joint. An exemplary method includes distracting the bone joint between the femoral head and the acetabulum or the glenohumeral joint.

DETAILED DESCRIPTION

Figure 1:
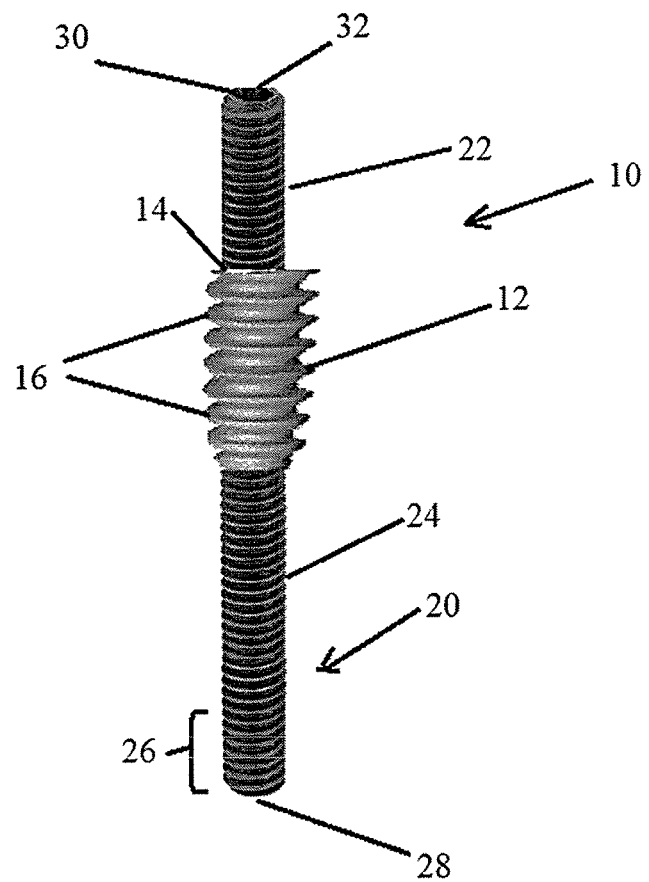
FIG. 1 is a perspective view of a fastener assembly of the present invention.

There is a need for an internal joint distracter and procedures which act to open and close the joint with lower force loads while avoiding peripheral nerve and tissue damage. Disclosed herein are medical devices and methods for internally distracting joints by using minimally invasive distraction. Distraction devices as disclosed herein can be used in medical procedures for treating, correcting, and/or repairing damage/diseased articular joints, e.g., avascular necrosis of the hip, arthritis in younger people, femoral-acetabular impingements (a condition where the hip bones have an abnormal shape), or Chondrolysis (gradual degradation of hyaline cartilage in the hip joint), worn or diseased aspects of the bones forming the joint.

In a disclosed embodiment, a distraction device is installed within a bone of a bone joint and force is applied to or by the device to distract the joint bones and separate and space articular surfaces from a joint socket.

In an embodiment, a tunnel is formed and can extend completely through a portion of one bone, and a distraction device is installed in the tunnel.

In another disclosed embodiment, twisting/rotating a component of a distraction device, e.g., a fastener, distracts the joint bones.

In still a further disclosed embodiment, applying a rotating force to a distraction device distracts joint bones.

In a disclosed embodiment for distracting a bone joint, a tunnel is formed in one bone of a bone joint, a fastener assembly is arranged within the tunnel, and a force is directly applied to a component of the fastener assembly to separate and distract the bones of the joint.

In a still further disclosed embodiment, a fastener assembly for joint distraction is installed in the greater trochanter.

In another disclosed embodiment, twisting/rotating a threaded shaft within a threaded cannulation distracts a joint.

In one disclosed fastener embodiment, a cannulated fastener is inserted and lodged in the greater trochanter, and a blunt, threaded screw or peg is inserted and twisted flush to the anterior inferior iliac spine on the pelvis. The threaded screw or peg is then twisted clockwise to achieve hip joint distraction In other disclosed fastener embodiments, a suture-anchor construct is deployed in the greater trochanter, and the suture is externally tensioned to distract the joint. The sutures can be attached to a tensioner on a treatment surgical/patient/table or bed which directly applies tension to the suture.

Another disclosed embodiment is a distraction kit that includes at least one distraction device which includes a cannulated fastener (anchor/sheath), a set of different sized cannulated fasteners, a force applicator or set of force applicators receivable within corresponding cannulations, and drive tools to engage the fastener and/or force applicator.

These and other embodiments of the invention will become apparent from the following detailed description when read in conjunction with the accompanying drawings and illustrated exemplary embodiments of the invention.

In the following detailed description, reference is made to various embodiments. It is to be understood that other embodiments may be employed, and that structural and logical changes may be made without departing from the scope of the disclosure herein.

FIG. 1 shows a first distraction device which includes fastener assembly 10 with a cannulated fastener 12 (anchor or sheath) component/element having internal threads 14 and external threads 16. Assembly 10 uses less force and causes less collateral damage than existing joint distraction systems. Threaded element 20 (force applicator or jack), e.g. a rod/shaft/screw/peg, is another component/element of the fastener assembly, and includes a shaft 22, with external threads 24, a distal tip 26 that has a blunt and non-threaded end 28. The element 20 includes a proximal end 30 that can be headless or include a head each of which is configured (32) to be engaged by a drive tool having a similarly configured tip, hex, star, square, etc. (not shown). Although the force applicator is illustrated to be a single/unitary externally threaded member, the force applicator can comprise a series of the same of different length sections that have complimentary distal and proximal ends to engage one another and provide an applicator whose length can be patient adjusted.

The external threads of the anchor/sheath are configured to permit rotational insertion, lodging and removal of the anchor or sheath within the greater trochanter or bone adjacent the bone joint to be distracted. The internal threads 14 correspond to and cooperate with external threads 24 so that rotation of element 20 advances the element 20 through the anchor/sheath fastener 12. One or more assemblies 10 can be provided in a kit which include different sized cannulated fasteners, the same of different sized force applicators 20, and drive tools to engage and rotate the cannulated fasteners and/or the force applicator.

Figure 2:
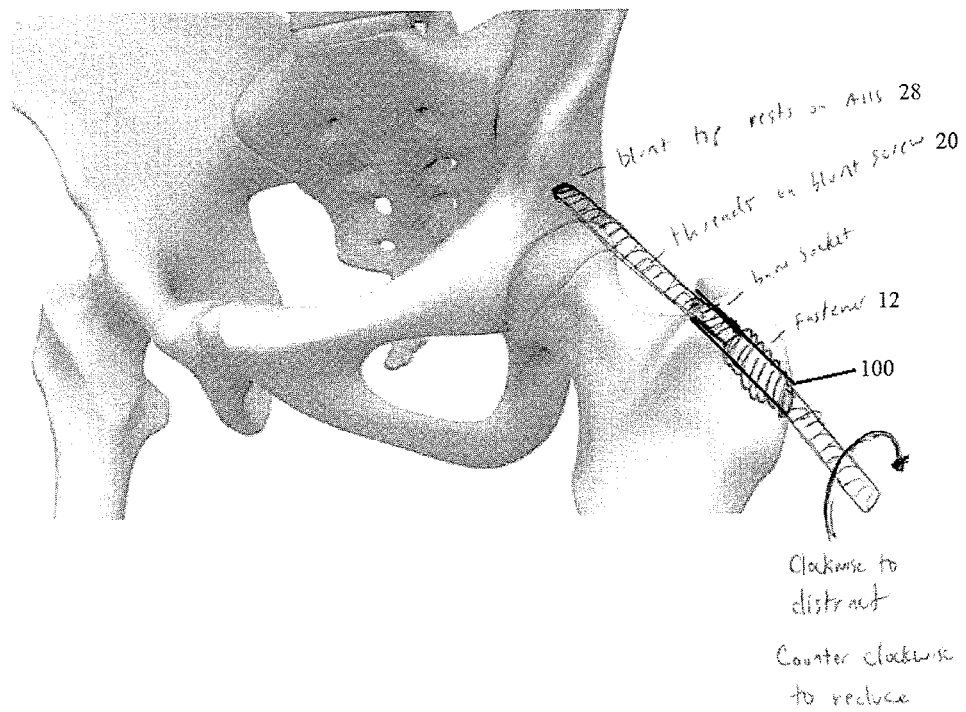
FIG. 2 is a perspective view of the fastener assembly of FIG. 1, deployed in the greater trochanter.

FIG. 2 illustrates distraction with the fastener that is inserted into a transosseous tunnel in and through the greater trochanter. The tunnel is prepared with a drill guide assembly, such as that used in various orthopedic procedures to efficiently and accurately position other surgical instrumentation relative to bone. A drill guide assembly that is used to prepare a hip joint for reconstructing the ligamentum teres, or other orthopedic procedures, including but not limited to, bone resurfacing procedures, joint replacement procedures, or other ligament reconstruction procedures, can be used. Suitable drill guides that confer the surgeon the ability to target bones from outside the joint, involving an alignment bar, such as that disclosed in U.S. Patent Publication No. 2014/0276841 or an articulating drill guide, such as that disclosed in U.S. Patent Publication No. 2014/0114322, may be used.

Once a transosseous tunnel 100 has been formed, rigid cannulated anchor or a sheath fastener 12 having internal threads 14 and external threads 16 is positioned, e.g., screwed into the tunnel. With the fastener assembly illustrated in FIGS. 1 and 2, the sheath or anchor 12 is rotated until the anchor or sheath 12 is fixedly positioned within the tunnel to a depth sufficient to permit the anchor or sheath 12 to function as a leverage point. Thereafter the blunt ended fastener is threaded into anchor or sheath 12 until end 28 engages the anterior inferior iliac spine 42 on the acetabulum 44. Further clockwise rotation/twisting of rod/shaft 20 separates the femoral head 52 from the anterior inferior iliac spine 42 on the acetabulum 44 to distract the joint 40. Once distracted, a medical practitioner may perform a desired medical procedure. Upon completion of the medical procedure, the rod/shaft 20 is twisted/rotated counter-clockwise to return the distracted femoral head to pre-surgical positions.

Although the present disclosure has been described in connection with preferred embodiments, many modifications and variations will become apparent to those skilled in the art. It should be understood that the above disclosure and embodiments therein are exemplary and are not to be considered as limiting.

What is claimed is:

1. A method of distracting a bone joint, comprising:
   forming a tunnel in one bone of a bone joint, wherein the bone joint is between a femoral head and an acetabulum;
   arranging a fastener assembly in the tunnel; and
   applying a force directly to a component of the fastener assembly to separate and distract the one bone from another bone of the bone joint, wherein the bone is the greater trochanter.

2. The method of claim 1, wherein the arranging a fastener assembly in the tunnel comprises first positioning a cannulated member within the tunnel.

3. The method of claim 2, further comprising inserting a force applicator into the positioned cannulated member.

4. The method of claim 3, wherein the force applicator comprises a blunt tip.

5. The method of claim 3, wherein the cannulated member is a cannulated anchor/sleeve.

6. The method of claim 1, wherein the arranging a fastener assembly in the tunnel comprises first positioning a cannulated member in the tunnel and then inserting a blunt tipped force applicator into the tunnel until it reaches the anterior inferior iliac spine on the acetabulum.

7. The method of claim 6, further comprising engaging the blunt tip of the force applicator with the anterior inferior iliac spine on the acetabulum and then rotating the force applicator so that the femoral head is distracted away from the acetabulum.

8. A joint distraction kit for performing the method of claim 1, wherein the joint distraction kit comprises a set of cannulated fasteners, a set of blunt tip force applicators, and drive tools to engage the fasteners and/or force applicators.

9. The kit according to claim 8, wherein the set of cannulated fasteners includes different sized fasteners.

10. The kit of claim 8, wherein the fasteners are cannulated anchors.

11. The kit of claim 8, wherein the fasteners are cannulated sheaths.

12. The kit of claim 8, wherein the force applicator includes a single shaft.

13. The kit of claim 8, wherein the force applicator comprises a plurality of interlocking sections.

14. A method of distracting a bone joint, comprising:
    forming a tunnel in a greater trochanter of a bone joint;
    arranging a fastener assembly in the tunnel; and
    applying a force directly to a component of the fastener assembly to separate and distract the greater trochanter from another bone of the bone joint.

15. A method of distracting a bone joint, comprising:
    forming a tunnel in a bone of a hip joint;
    arranging a fastener assembly in the tunnel; and
    applying a force directly to a component of the fastener assembly to separate and distract the bone from another bone of the hip joint, wherein the bone is the greater trochanter.

* * * * *